United States Patent [19]

Brown et al.

[11] Patent Number: 4,871,664
[45] Date of Patent: Oct. 3, 1989

[54] TYPE II RESTRICTION ENDONUCLEASE DSA I WITH PROCESS FOR OBTAINING IT AND THE USE THEREOF

[75] Inventors: Nigel L. Brown, Sea Mills; Anthony E. Walsby, Stoke Bishop, both of England

[73] Assignee: Boehringer Mannheim GmbH, Mannheim, Fed. Rep. of Germany

[21] Appl. No.: 12,192

[22] Filed: Feb. 9, 1987

[51] Int. Cl.$^4$ .................. C12P 19/34; C12N 9/22; C12R 1/01
[52] U.S. Cl. ..................... 435/91; 435/199; 435/822
[58] Field of Search ............ 435/199, 91; 536/27

[56] References Cited

PUBLICATIONS

Walsby, A. E., et al, (1983), Proc. R. Soc Lond. 217, 417–447.
Kessler, C. et al., (1985), Gene, 33, pp. 1, 14, 25, 68–70.
Mise, K., et al. (1985), Gene, 33, 357–361.

*Primary Examiner*—Thomas G. Wiseman
*Assistant Examiner*—Charles L. Patterson, Jr.
*Attorney, Agent, or Firm*—Felfe & Lynch

[57] ABSTRACT

The present invention provides a type II restriction endonuclease isolated from *Dactylococcopsis salina*. The endonuclease is known as Dsa I, and recognizes the following nucleotide sequence and has a cleavage point indicated by the arrows:

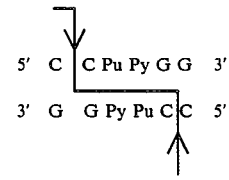

Also described is a process for obtaining Dsa I from *D. salina*.

8 Claims, No Drawings

TYPE II RESTRICTION ENDONUCLEASE DSA I WITH PROCESS FOR OBTAINING IT AND THE USE THEREOF

The present invention is concerned with a new Type II restriction endonuclease, Dsa I, with a process for obtaining it and with the use thereof.

Type II restriction endonucleases are endodeoxyribonucleases which are able to recognize certain DNA sequences and to cleave them. Phosphodiester bridges are thereby hydrolyzed in the target sequence, namely, one in each polynucleotide strand. Therefore, Type II restriction endonucleases are valuable for the analysis of DNA molecules.

Admittedly, specific Type II restriction endonucleases are already known for numerous DNA sequences but there is still a need for further Type II restriction endonucleases which are specific for DNA sequences which have hitherto not been recognized by any of the known restriction endonucleases.

Therefore, it is an object of the present invention to provide a new restriction endonuclease which specifically recognizes and cleaves a sequence which has hitherto not been recognized by any such enzyme.

Thus, according to the present invention, there is provided a restriction endonuclease which is characterized by the recognition sequence:

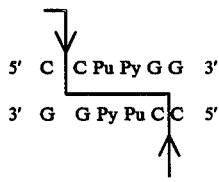

Pu (purine) means A or G (adenine or guanine) and Py (pyridine) means T or C (thymine or cytosine).

This enzyme preferentially cleaves at the point of cleavage defined by the arrow but other points of cleavage within this sequence are also possible.

The new Type II restriction endonuclease according to the present invention, which in the following is called Dsa I, has a temperature optimum around 37° C. The best buffer conditions for the enzyme are around pH 8.8. The enzyme has good activity between pH 8.5 and 9.0 with a monovalent cation concentration optimum around 100 mmol/l (using NaCl) in 10 mmol/l $MgCl_2$ and 10 mmol/l 2-mercaptoethanol. An enzyme which is isochizomeric to Dsa I is not known.

The enzyme acts on the following hexanucleotide doublestranded sequences:

| 5' C C A T G G 3' | 5' C C G C G G 3' |
| 3' G G T A C C 5' | 3' G G C G C C 5' |
| 5' C C A C G G 3' | 5' C C G T G G 3' |
| 3' G G T G C C 5' | 3' G G C A C C 5' |

The recognition sequence can be confirmed by the complete breakdown of the DNAs of the virus SV40 and Adeno 2, the phages lambda, phiX 174, phage-derivative M13 mp7 and the plasmid pBR322.

These DNA molecules were digested with Dsa I and the number of experimentally determined cleavage sites are shown in Table I.

TABLE I

Comparison of experimentally observed cleavage specificity with the computer-search for a cleavage specificity of an enzyme recognizing C/CPuPyGG.

| DNA | Number of experimentally observed cleavage sites | Number of cleavage sites obtained by computer search | experimentally observed fragment lengths | Fragment lengths obtained by computer search | Cleavage positions obtained by computer search |
|---|---|---|---|---|---|
| SV40 | 3 | 3 | 4700 | 4720 | 269 |
|  |  |  | 300 | 296 | 469 |
|  |  |  | 230 | 227 | 5216 |
| phiX174 | 3 | 3 | 2300 | 2323 | 1415 |
|  |  |  | 1600 | 1619 | 2859 |
|  |  |  | 1500 | 1444 | 5182 |
| M13mp7 | 2 | 2 | 3800 | 3842 | 2763 |
|  |  |  | 3400 | 3396 | 6605 |
| pBR322 | 2 | 2 | 3500 | 3444 | 528 |
|  |  |  |  | 900 | 919 | 1447 |

The experimentally determined number of cleavage sites are identical to the number of cleavage sites obtained by computer-search of the various DNAs for the sequence CCPuPyGG (Table I). In addition the data are comparable to the tables of Gene 10: 357-370 (1980). Double digests of pBR322 and phiX174 DNAs with Hinf I and Dsa I and of SV40 DNA with Rsa I and Dsa I confirm that the specificity is CCPuPyGG.

For the analysis of the position of the cleavage site within the recognition sequence there was selected a suitable site in the DNA sequence of Tn501 (Nucl. Acids Res 13 (1985) 5657-5669).

A M13 mp7 recombinant DNA [DNA of M13 mp7 RF (cf. Nucl. Acids Res. 9 (1981) 309-321) carrying a DNA fragment consisting of nucleotides 5333 through 5633 of Tn 501, and coding for Dsa 1 was used, and the cleavage site in the Dsa I recognition site at position 5381 of Tn501 was determined by the method according to Meth. Enzymol. 65 (1980) 391-404 in conjunction with dideoxynucleotide sequencing. The cleavage specificity at this site was shown to be 3'-/CACGG-5'. The general cleavage specificity is therefore 3'-C/CPuPyGG-5'.

According to the present invention, Dsa I is obtained by culturing Dactylococcopsis salina and recovering the enzyme from the cells. For obtaining the enzyme, there can be used the conventional biochemical purification methods, whereby, in particular fractions obtained, the presence of the enzyme can easily be demonstrated on the basis of the cleavage of its recognition sequence. As substrate, there can be used, for example, lambda DNA. The DNA fragments obtained are separated electrophoretically in agarose gels in the buffer systems conventional for the fragment separation in the presence of ethidium bromide.

The micro-organisms Dactylococcopsis salina used for obtaining the enzyme grows aerobically as described in Proc. Roy. Soc. Lond. B217 (1983) 417–447, except that the medium is modified to contain 7.8 mg $K_2HPO_4$ per liter instead of 15 mg. The light intensity used is about 20 uE $m^{-2}sec^{-1}$.

Dactylococcopsis salina has been deposited at the Deutsche Sammlung von Mikroorganismen Gesellschaft für Biotechnologische Forschung mBH Grisebachstrasse 8, 3400 Göttinger, Federal Republic of Germany and bears Accession Number DSM 4080.

The enzyme is isolated and purified from the culture by using conventional mechanical and chemical methods, for example high pressure dispersion, ultrasonics or enzymatic digestion.

In a preferred embodiment of the process according to the present invention the cells are pressurized to 5 bar to form a cell paste. Then the cell paste is resuspended in phosphate-buffer (pH 7.4) containing protease inhibitors, sonicated and centrifuged at 100,000 g. Further purification of the supernatant is preferably conducted by molecular sieve fractionation, chromatography over ion exchanges as well as subsequent affinity chromatography. Exemplary of cation exchangers is the product commercially available under the name phosphocellulose P11 (Whatman), and as anion exchanger is the product commercially available under the name DEAE Sephadex (Pharmacia). Other useful cation and anion exchangers will be recognized by one skilled in the art.

Isolation, identification and characteristics of *Dactylococcopsis Salina* are the same as already described in *Proc. Roy. Soc.* supra, whose disclosure is herewith incorporated in this disclosure.

The following discussion of "Isolation", "Identification", "Culture" and "Characteristics" of *D. salina* are taken from the *Proc. Roy. Soc.* paper cited supra.

Isolation

Work on the Solar Lake (Sinai) was done from an inflatable boat tethered over the deepest part to a steel wire strung across the lake. Water temperature was measured with a submersible thermistor probe. Light intensity was measured with a Lambda QRP 361 underwater quantum meter sensitive to photosynthetically active radiation between wavelengths of 400 and 700 nm.

Water samples were collected by lowering the end of a weighted polyethylene tube to a specified depth and drawing water up with an electrically driven peristaltic pump. After discarding twice the dead volume of water in the tubing, samples were collected in brown glass bottles shaded from direct sunlight. The samples were transported back to a laboratory at Elat for chemical analyses and measurements on the suspended microorganisms, done on the same day. Salinity was determined by refractometry. Samples were collected separately in glass stoppered bottles for subsequent analysis of dissolved oxygen, by Winkler titration, and dissolved sulphide by the method of Cline, Limnol. Ocenog. 14: 454–458 (1969).

The photosynthetic capacity of cell suspensions from cultures or the lake water was measured by incubating samples in the presence of $NaH^{14}CO_3$ of known specific activity, filtering through glass fiber filters (Whatman GF/C), removing inorganic carbon by exposure to fuming HCl, suspending in Packard Insta Gel and then counting in a liquid scintillation counter.

The concentration of Dactylococcopsis cells in the lake water was determined by placing 5 ml samples in 20 mm diameter sedimentation chambers allowing the cells to sediment overnight after addition of Lugol's iodine, and then counting the number of cells in sample fields of view under the inverted microscope. Initially, samples were first pressurized to collapse gas vacuoles and ensure sedimentation but it was subsequently found that collapse occurred anyway after iodine treatment.

Cultures of *Dactylococcopsis salina* were maintained in 250 ml Erlenmeryer flasks containing 100 ml of culture medium (described in §3b) in thermostatted culture cabinets at 34° C. under illumination from warm white fluorescent lamps.

Identification

Microscopical examination of Solar Lake water samples taken in early April 1979 revealed the presence of a previously described gas-vacuolate cyanobacterium with the following features. It was unicellular with the fusiform cells measuring 4–8 $\mu m$ in width, dividing transversely. Single cells varied from 35 to 80 $\mu m$ in length and dividing or paired cells were up to 135 $\mu m$ long. Where a cell had just divided a hemispherical end was left. The distal end was pointed. Both ends were pointed in longer (and hence older) cells, indicating a change in end shape with maturation.

Gas vacuoles were present along the cell margins and were usually most abundant at the ends of the cell, and particularly at the older, more pointed end. The identity of the gas vacuoles was confirmed by their disappearance under pressure (Walsby, Arch. Hydrobiol 74: 375–392 (1974).

The cytoplasm of the cells contained extensive clear areas, subsequently shown by electron microscopy to be distended intralamellar vesicles. These were less marked in cells collected later in the year at greater depth in the lake and may be a particular feature of the cells grown at high light intensity. Other variable features of the cells, such as pigmentation and shape, were also observed when the organism was grown in culture.

Under the taxonomic system of Geitler, *L. Rabenhorst's Kryptogamen-flora* vol. 18 Leipzig: Akademische Verlags Gesellschaft (1932) the organism keys out firmly in the genus Dactylococcopsis. It most closely resembles in shape the species Dactylococcopsis(-=*Myxobactron*)*hirudiforme* West (West, Ann. S. Afr. Mus. 9: 61–90 (1912). This organism is reported to be of different dimensions and occurred "in the tank of the cable station at Mossamedes", which would presumably have contained fresh water. The Solar Lake organism will not grow at salinities below that of sea water. Gas vacuoles have not previously been reported in Dactylococcopsis and in Geitler's alternative key the presence of gas vacuoles would preclude the organism from this genus. However, the presence or absence of gas vacuoles is not now considered to be a good primary criterion for taxonomic separation (see Walsby, In, Starr, ed. *The Prokaryotes* Berlin: Springer-Verlag pp. 224–235 (1981). The name *Dactylococcopsis salina* has been proposed for the organism.

Culture

Samples of lake water taken from a depth of 1 m where the organism was most abundant were inoculated into culture medium similar to the one described below but made up in filtered sea water. From this a culture of Dactylococcopsis was established. It grew well at temperatures exceeded 30° C., and 34° C. was adopted for subsequent maintenance of cultures. The first cultures were contaminated with green flagellates. These were eliminated by low speed centrifugation: buoyant filaments of Dactylococcopsis were accelerated to the water surface from which they could be withdrawn free of other, non-buoyant cells (see Walsby (1981) for details of the method).

The composition of the culture medium finally adopted for growth of the organism was as follows. In 1 l of water was dissolved NaCl (125 g), $MgCl_2.6H_2O$ (10 g), $MgSO_4.7H_2O$ (3.5 g) KCl (2.5 g), $NaNO_3$ (0.75 g), $CaCl_2.2H_2O$ (0.5 g), $K_2HPO_4$ (15 mg), $Na_2CO_3$ (20 mg), disodium $EDTA.2H_2O$ (0.5 mg), ferric ammonium citrate (3 mg), citric acid (3 mg) and 0.1 ml of the trace-metal mix A5 described by Stanier et al. Bact. Rev. 35: 171-205 (1971).

Growth of Dactylococcopsis was also obtained on solid media. The best results were obtained with low concentration (0.6%) agar plates on which Dactylococcopsis formed elongate sinusoidal or sickle-shaped green colonies. The strain currently maintained in culture was grown from a single cell separated colony. The culture is unicyanobacterial but not yet free of a contaminating bacterium that occurs in very low numbers in actively growing cultures.

This is the first report of a species of Dactylococcopsis being grown in culture.

Characteristics of Dactylococcopsis in Culture

The cell retained in a similar shape in culture to those seen in the lake. At low light intensity (20–30 $\mu E + m^{-2}S^{-1}$) the cultures were a milky blue-green, becoming more transparent after collapse of gas vacuoles by pressure. The culture became yellow-orange at high light intensities and when starved of nitrogen; it then resembled in color lake samples concentrated by filtration. The absorption spectrum of a suspension of the blue-green colored cells, broken by ultrasonication and clarified by centrifugation, showed two main peaks in the visible region, at 620 nm diagnostic of phycocyanin, and at 670 nm diagnostic of chlorophyll $\alpha$. The carotenoid:chlorophyll $\alpha$ ratio of cells grown at low light intensity, determined by the method of Strickland & Parsons (1968), was 0.4. In cells grown at higher intensities (130 $\mu E \, m^{-2}S^{-1}$), and those collected from the lake, the ratio was 1.0 to 1.2.

Cells occur singly or in pairs separating after division except when cultured in medium of reduced salinity (<1 M NaCl), when short chains are produced owing to incomplete constriction at the cell ends. Cells grown at low light intensities (8.6 $\mu E \, m^{-2}S^{-1}$) were filled with dense blue-green cytoplasm. As these cultures aged the individual cells appeared paler and some developed intensely blue granules which fluoresced bright red when illuminated with green light from a Leitz Ploemopak fluorescence illuminator (with a BP 546/14 excitation filter and a LP 580 suppression filter). The granules were presumably local aggregations of phycocyanin. Gas vacuoles were located mainly at the cell periphery, giving the cells a rather ragged outline. The cells grown at high light intensities contained large clear areas and enlarged intralamellar vesicles, and more resembled the form encountered in the lake.

The following Examples are given for the purpose of illustrating the present invention:

EXAMPLE 1

Dactylococcopsis salina is cultured at 34° C. at a light intensity of about 20 uE $m^{-2}sec^{-1}$ and harvested in the late log or stationary phase. The culture medium has the composition as described in Proc. Roy. Soc. supra, except that the medium contains 7.8 mg/l $K_2HPO_4$ instead of 15 mg/l.

The culture was pressurized to 5 bar to disrupt the gas vesicles before the cells can be centrifuged to form a cell paste.

The cell paste was resuspended in three vols PC buffer (10% glycerol (w/v), 10 mmol/l potassium phosphate, pH 7.4, 1 mmol/l EDTA, 10 mmol/l 2-mercaptoethanol) containing protease inhibitors, sonicated at 60 W for 30×30 secs, and centrifuged at 100,000 g for 60 minutes. The supernatant was then diluted in an equal volume of PC buffer (+inhibitors) to reduce the salt concentration, and loaded onto phosphocellulose P11. A gradient of 0–1.0 mol/l KCl in PC buffer was used. DsaI was found in the fractions eluting between 0.65 and 0.85 mol/l KCl.

The active fractions are combined and dialyzed against TRIS/HCl buffer (pH 8.8) containing 10 mmol/l 2-mercaptoethanol, 100 mmol/l sodium chloride, 10 mg/l magnesium chloride and 50% (v/v) glycerol.

Activity determination:
Unit definition:
1 U DsaI completely cleaves 1 $\mu g$ lambda DNA within 1 hour at 37° C. in 25 $\mu l$.

Into a mixture of 12 $\mu l$ incubation buffer, containing 0.02 mol/l TRIS/HCl, pH 8.8/37° C., 0.02 mol/l magnesium chloride, 0.2 mol/l sodium chloride and 0.02 mol/l 2-mercaptoethanol are introduced 7 $\mu l$ water and 5 $\mu l$ lambda DNA [(4 OD/ml extinction (optical density)], as well as 1 $\mu l$ DsaI solution (1 U/$\mu l$). The solution is maintained at 37° C. for 1 hours, cooled on ice and mixed with 5 $\mu l$ of a stop solution containing 7 mol/l urea, 20% (w/v) saccharose, 0.06 mol/l EDTA and 0.01% w/v bromphenol blue. It is then separated electrophoretically on 1% agarose gel for 3 to 4 hours at 100 V. The bands obtained are identified in comparison with DNA length standards.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the spirit and scope of the invention.

We claim:

1. Type II restriction endonuclease recognizing all nucleotide sequences defined by

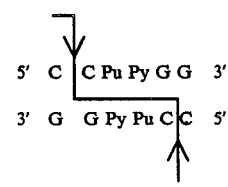

and having a cleavage position defined by the arrows.

2. Type II restriction endonuclease of claim 1 having a temperature optimum around 37° C. and a pH optimum between 8.5 and 9.0.

3. Type II restriction endonuclease of claim 1, obtained from *Dactylococcopsis salina* (DSM 4080).

4. Method for obtaining a Type II restriction endonuclease having a recognition sequence

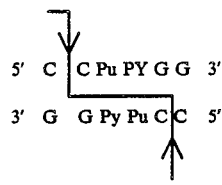

and a cleavage position indicated by the arrows comprising culturing a sample of Dactylococcopsis salina DSM 4080 under conditions favoring production of said endonuclease and separating said endonuclease therefrom.

5. Method of claim 4, comprising subjecting said sample to a pressure of 5 bar to form a cell paste, suspending said cell paste, sonicating the suspension, separating insoluble materials from said suspension and leaving a supernatant, contacting said supernatant to a cation exchanger under conditions favoring separation of said endonuclease therefrom and collecting said endonuclease.

6. Method for obtaining a DNA fragment with the terminal sequence

```
5' C
3' G G Py Pu C 5'
or
5' C Pu Py G G 3'
```
-continued
```
3'           C 5'
``` comprising contacting a sample of DNA containing the sequence

```
5' C C Pu Py G G 3'
3' G G Py Pu C C 5'
``` with a type II restriction endonuclease recognizing all nucleotide sequences defined by

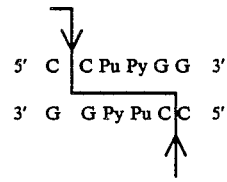

and having a cleavage position indicated by the arrows under conditions favoring cleavage of said DNA by said endonuclease and separating said fragment from said sample.

7. Method of claim 6, wherein said endonuclease is obtained from *Dactylococcopsis salina* (DSM 4080).

8. Method of claim 6, wherein said endonuclease is contacted to DNA with sequence:

| | |
|---|---|
| 5' C C A T G G 3' | 5' C C G C G G 3' |
| 3' G G T A C C 5' | 3' G G C G C C 3' |
| 5' C C A C G G 3' | 5' C C G T G G 3' |
| 3' G G T G C C 5'    or | 3' G G C A C C 5'. |

* * * * *